(12) United States Patent
Yang

(10) Patent No.: US 7,101,338 B2
(45) Date of Patent: Sep. 5, 2006

(54) SPHYGMOMANOMETER WITH THREE-DIMENSIONAL POSITIONING FUNCTION

(75) Inventor: Paul Yang, Taipei (TW)

(73) Assignee: Health & Life Co., Ltd., (TW)

( * ) Notice: Subject to any disclaimer, the term of this patent is extended or adjusted under 35 U.S.C. 154(b) by 0 days.

(21) Appl. No.: 10/843,341

(22) Filed: May 12, 2004

(65) Prior Publication Data

US 2005/0256411 A1 Nov. 17, 2005

(51) Int. Cl.
*A61B 5/02* (2006.01)

(52) U.S. Cl. ............... 600/485; 600/490; 600/500; 600/503

(58) Field of Classification Search ........... 600/485, 600/490, 493–496, 500–503
See application file for complete search history.

(56) References Cited

U.S. PATENT DOCUMENTS

| | | | | |
|---|---|---|---|---|
| 4,429,699 | A * | 2/1984 | Hatschek | 600/494 |
| 5,778,879 | A * | 7/1998 | Ota et al. | 600/485 |
| 6,251,080 | B1 * | 6/2001 | Henkin et al. | 600/490 |
| 6,547,741 | B1 * | 4/2003 | Mori et al. | 600/490 |
| 6,712,769 | B1 * | 3/2004 | Freund et al. | 600/503 |
| 6,856,327 | B1 * | 2/2005 | Choi | 345/684 |
| 6,872,182 | B1 * | 3/2005 | Kato et al. | 600/490 |
| 2004/0199081 | A1 * | 10/2004 | Freund et al. | 600/485 |

* cited by examiner

*Primary Examiner*—Robert Nasser, Jr.
(74) *Attorney, Agent, or Firm*—Bacon & Thomas PLLC

(57) ABSTRACT

The present invention discloses a sphygmomanometer having 3D positioning function, which comprises a microprocessor chip which is coupled individually to a microprocessor chip which is coupled individually to a pressure sensor, an alarm unit, a storing unit, a 3D acceleration sensor chip, a display device, a driving device, and an air valve, so that when a person's blood pressure is measured, the 3D acceleration sensor chip detects the spatial position of the measuring cuff of the sphygmomanometer and sends the parameters related to the detected spatial position to the microprocessor chip. In the meantime, the microprocessor chip will retrieve a predetermined range of the parameters related to the spatial position from the storing unit, and compare such range with the value of the detected parameters. If the values of the detected parameters fall beyond the predetermined range of parameters, the microprocessor chip will issue an alarm through the alarm unit until the spatial position is correct. Thus the person who takes blood pressure measurement can always get the most accurate measurement.

6 Claims, 6 Drawing Sheets

SPHYGMOMANOMETER WITH THREE-DIMENSIONAL POSITIONING FUNCTION

BACKGROUND OF THE INVENTION

1. Field of the Invention

The present invention relates to a sphygmomanometer with a three-dimensional (3D) positioning function, more particularly to a sphygmomanometer which uses a 3D acceleration sensor chip to detect the spatial position of a measuring cuff of the sphygmomanometer and send the parameters of the detected spatial position to the chip processor, such that after the comparison of the parameters, the tester can move the measuring cuff of the sphygmomanometer or the posture of a related part of the tester body to the correct spatial position.

2. Description of the Related Art

In general, sphygmomanometers are divided into a traditional mercury type and an electronic type; wherein the mercury type is not only time-consuming, but it also requires professionally trained and experienced people to correctly measure a blood pressure. On the other hand, electronic sphygmomanometers are further divided into a desktop type, a wrist type, a tunnel type and a finger type, etc. Since it is not necessary to calibrate the electronic sphygmomanometer beforehand, and the result of the measurement is displayed on a display device, its use is simple and convenient to users. Although electronic sphygmomanometers have the foregoing convenience, yet as we all know that the result of blood pressure measurement not only depends on the time of performing the measurement, but also depends on the spatial position of the measuring wrist or the related part of the tester's body. For example, the blood pressure in the morning is generally lower than the blood pressure in the afternoon, and the correct position for putting the measuring cuff of a wrist sphygmomanometer for measuring blood pressure should be level with the heart. Generally, people cannot determine whether or not the measuring cuff of the wrist sphygmomanometer has been lifted to the correct spatial position, and the present wrist sphygmomanometer does not provide the three-dimensional positioning function, but only bases on one's experience to move the sphygmomanometer in different directions such as up and down or left and right. Such doing often causes inaccurate measurement of the blood pressure.

SUMMARY OF THE INVENTION

In view of the shortcomings of the prior-art structure, the inventor of the present invention focused on the crux of the problem and started seeking improvements to overcome the shortcomings and pursue a feasible solution. After extensive researches, analyses, and designs, the inventor invented the sphygmomanometer with a three-dimensional (3D) positioning function.

The primary objective of the present invention is to provide a sphygmomanometer having a 3D positioning function, and the sphygmomanometer comprises a microprocessor chip, and the microprocessor chip is coupled individually to a storing unit, and a 3D acceleration sensor chip. When the sphygmomanometer according to the present invention is in use, the 3D acceleration sensor chip detects the spatial position of the measuring cuff of the sphygmomanometer and then sends the parameters of the spatial position to a microprocessor chip. In the meantime, the microprocessor chip will retrieve a predetermined range of the related parameters from a storing unit for the comparison with the parameters for the detected spatial position. If the values of the detected parameters fall beyond the predetermined range of related parameters, then the position of the measuring cuff of the sphygmomanometer or the related part of the tester's body is incorrect. The microprocessor chip will issue an alarm through an alarm unit to alert the tester to move the measuring cuff of the sphygmomanometer to a position until the values of the parameters for the spatial position fall within the predetermined range, and then the alarm unit will stop the alarm message. In other words, the position of the measuring cuff of the sphygmomanometer or the related part of the tester's body has been placed in a correct position. Therefore, the blood measurement taken by a user will be more accurate.

Another objective of the present invention is to provide a sphygmomanometer having 3D space positioning function, wherein its control circuit is connected to a display device, so that when the sphygmomanometer is in use, the display device can display the result of the tester's blood pressure measurement.

Another objective of the present invention is to provide a sphygmomanometer having 3D space positioning function, wherein its 3D acceleration sensor chip is a semiconductor chip comprised of a piezoelectric transformer (PZT), a bridge type sensor and a corresponding electronic device, and a plumb bob disposed on the piezoelectric transformer, and a seating extended from the X-axis, Y-axis and Z-axis of the plumb bob will shake as the spatial position changes. The seating is connected to the bridge type sensor, such that the seating moves according to the measuring cuff worn by the tester, and if the seating is inclined to different angles, the piezoelectric transformer will produce a change of voltage. The bridge type sensor will send such change to the microprocessor chip and convert it into a spatial position related parameter. The microprocessor chip will retrieve the predetermined range of the values for the spatial position related parameters from the storing unit and compare such values with the values of the detected spatial position parameters. If the detected value of the related parameters fall beyond the range of the values of related parameters, then the spatial position of the measuring cuff of the sphygmomanometer or the position of the related part of the tester's body is incorrect, and will notice the tester to move the measuring cuff to a correct position or adjust the posture of the related part of the user's body until the values of measured parameter fall within the predetermined range of the related parameters.

BRIEF DESCRIPTION OF THE DRAWINGS

To make it easier for our examiner to understand the objective of the invention, its structure, innovative features, and performance, we use a preferred embodiment together with the attached drawings for the detailed description of the invention.

DETAILED DESCRIPTION OF THE INVENTION

Figure 1:
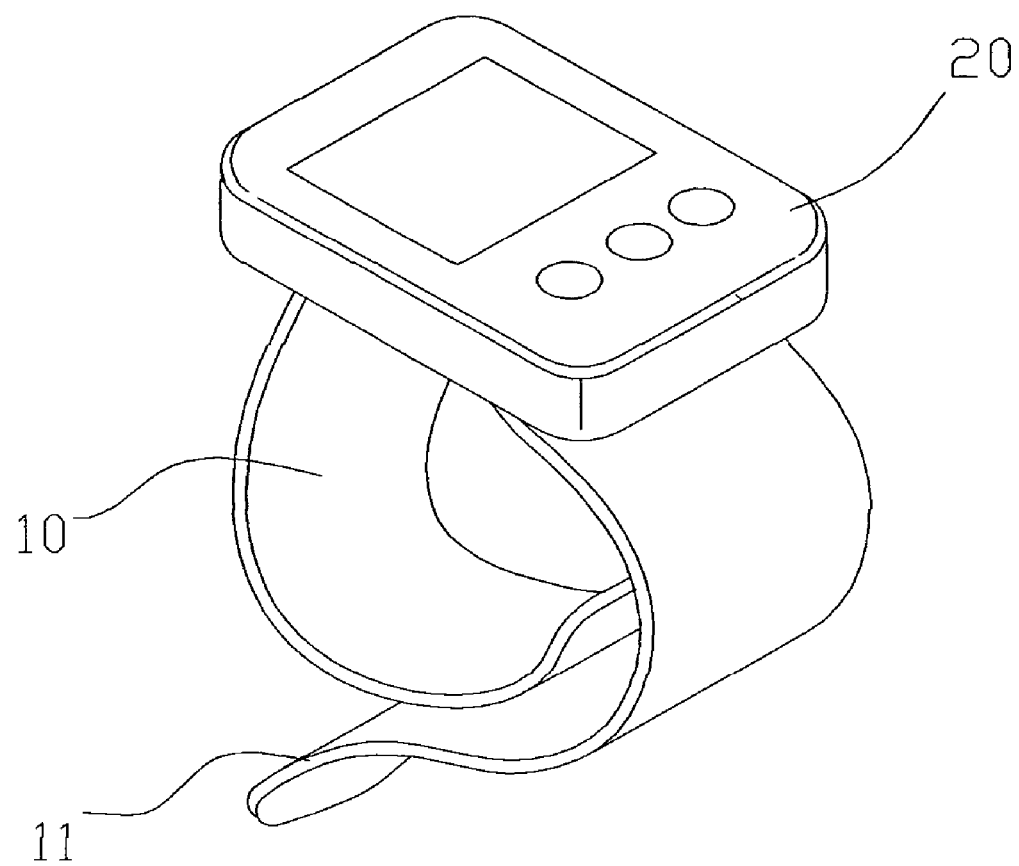
FIG. 1 is a perspective view of the sphygmomanometer of the present invention.
Figure 2:
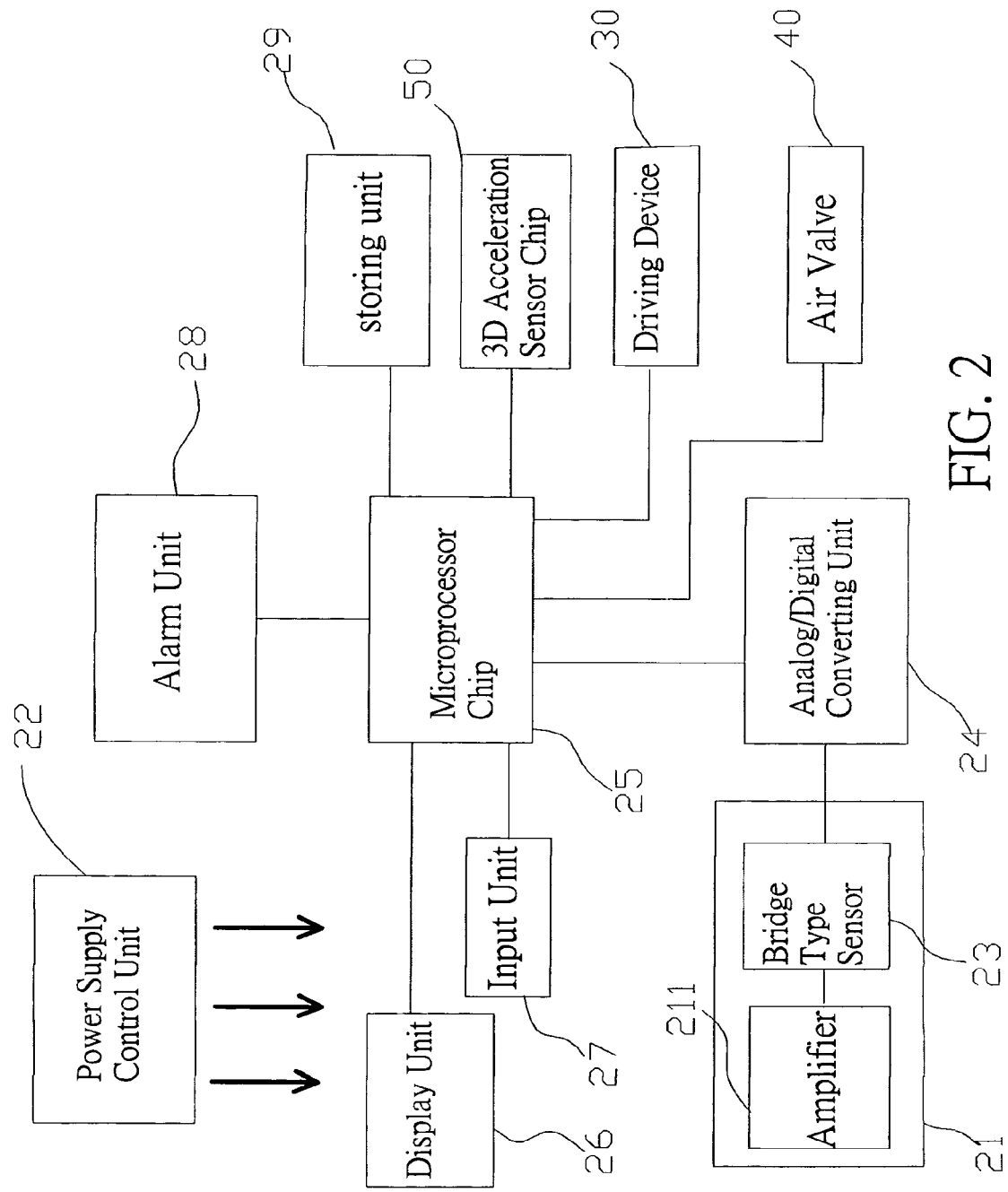
FIG. 2 is schematic circuit diagram of the sphygmomanometer according to a preferred embodiment of the present invention.
Figure 3:
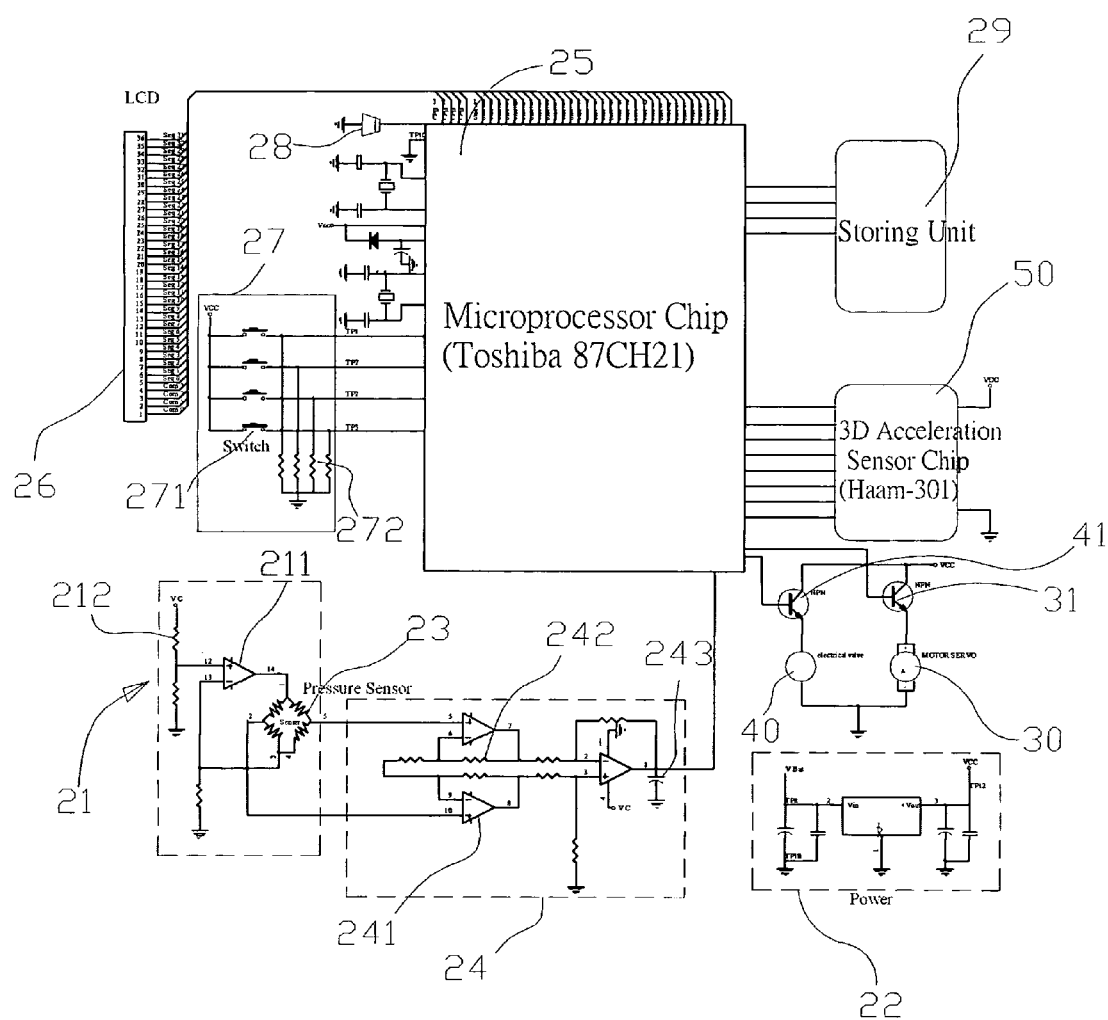
FIG. 3 is a schematic circuit diagram of the sphygmomanometer according to a preferred embodiment of the present invention.
Figure 4:
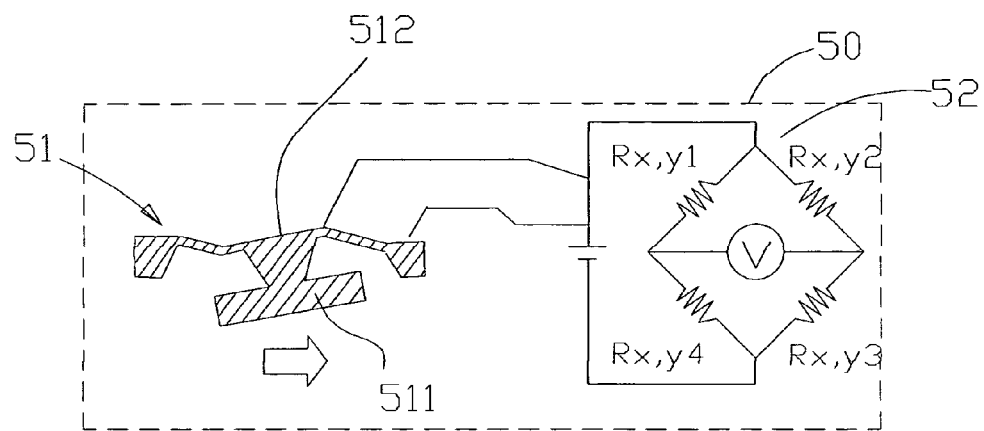
FIG. 4 is a structural diagram of the X-axis and Y-axis of the piezoelectric transformer and the bridge type sensor in the 3D acceleration sensor chip of the present invention.
Figure 4A:
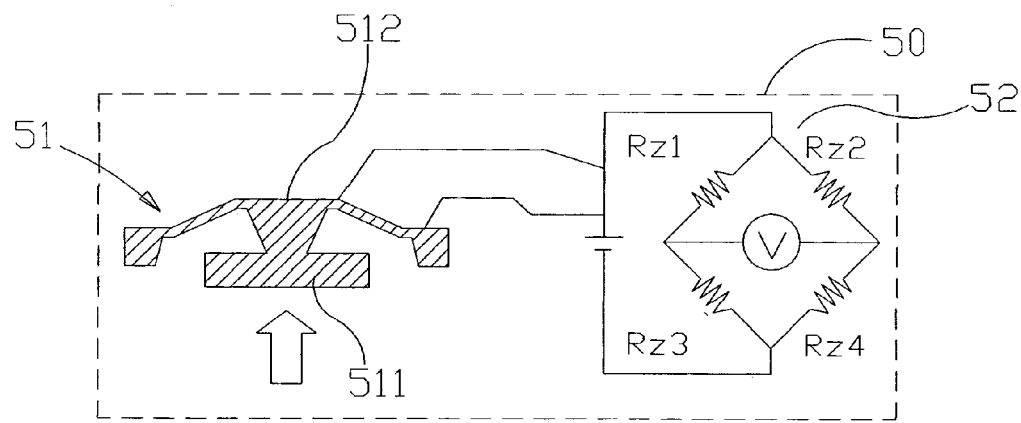
FIG. 4A is a structural diagram of the Z-axis of the piezoelectric transformer and the bridge type sensor in the 3D acceleration sensor chip of the present invention.
Figure 5:
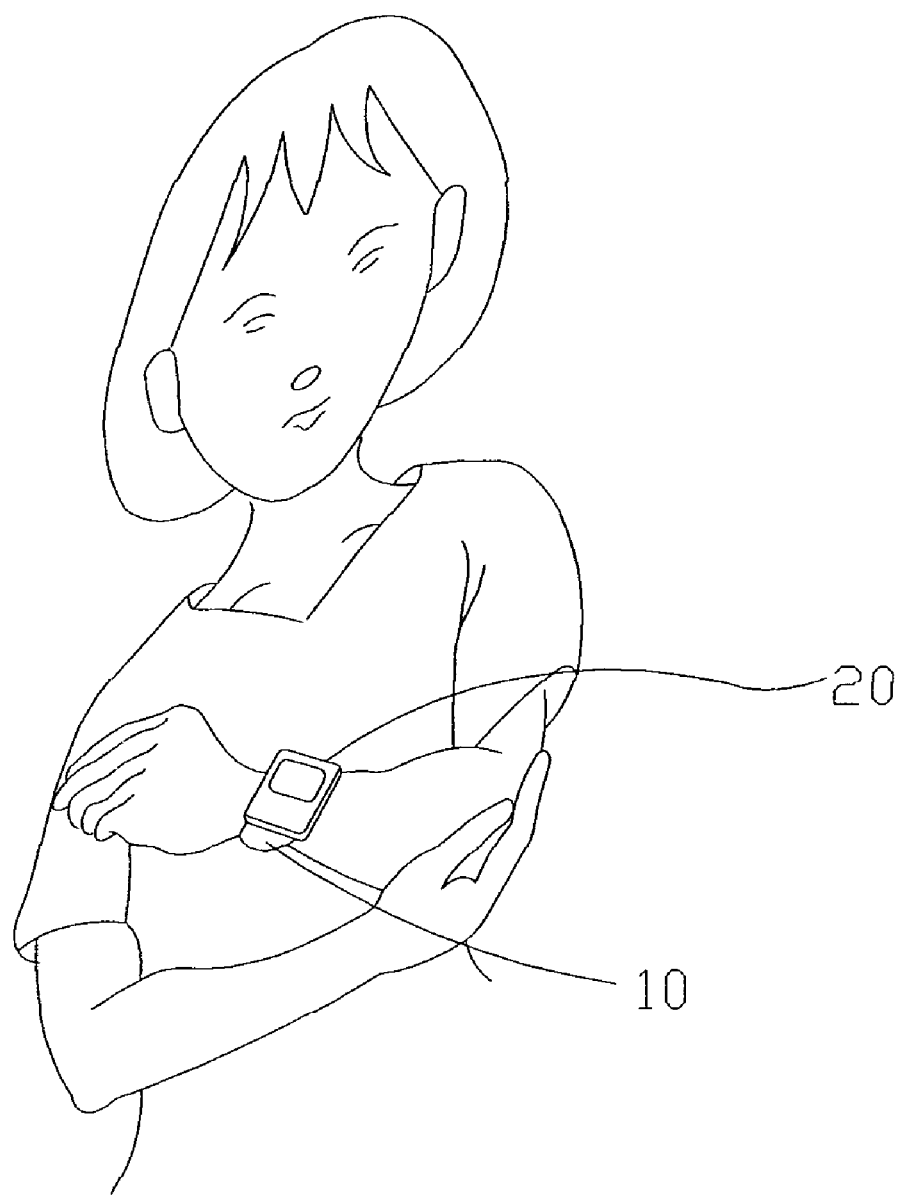
FIG. 5 is a view of the motions taken when a tester uses a wrist sphygmomanometer to measure blood pressure according to the present invention.
Figure 5B:
FIG. 5B is a view of the motions along the Z-axis when a user uses a wrist sphygmomanometer to measure blood pressure according to the present invention.
Figure 5A:
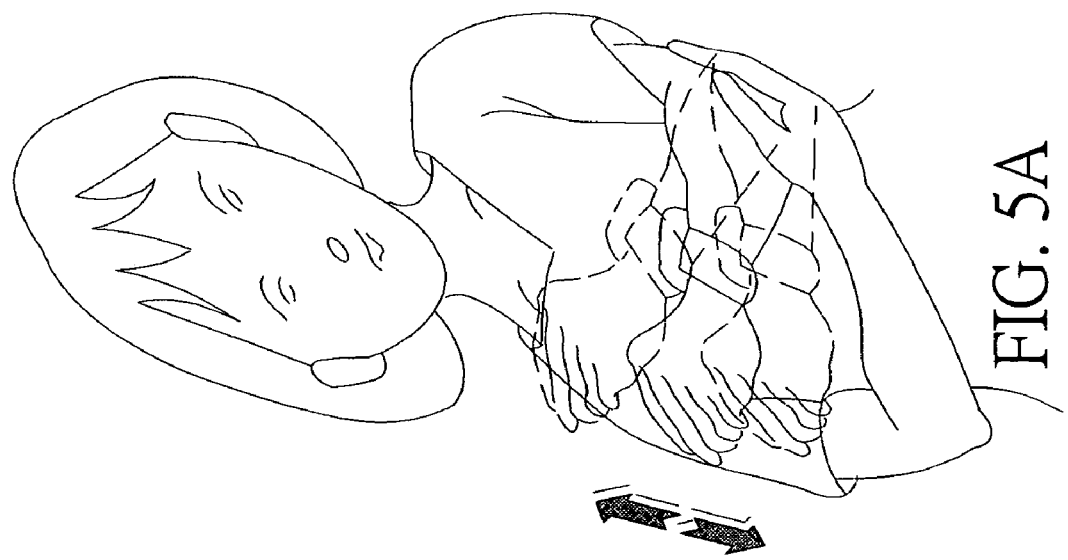
FIG 5A is a view of the motions along the X-axis and Y-axis when a tester uses a wrist sphygmomanometer to measure blood pressure according to the present invention.

Please refer to FIGS. 1, 2 and 3 for the sphygmomanometer having 3D space positioning function, and the invention uses a wrist sphygmomanometer for example. The sphygmomanometer comprises an airbag cuff 10, an adhesive tape 11 individually adhered on both ends of the airbag cuff 10 for the adhesion, a housing 20 disposed on the airbag cuff, and a pressure sensor 21 disposed in the housing 20. A pressure difference is used to detect a change in blood pressure. Such pressure sensor 21 includes an amplifier 211 and a bridge type sensor 23; wherein the input end of the amplifier 211 is connected to a power supply unit 22 and a resistor 212, and the output end of the amplifier 211 is connected to the bridge type sensor 23, such that the result detected by the pressure sensor 21 is amplified by the amplifier 211, and the voltage is outputted by the bridge type sensor 23.

The bridge type sensor 23 is also connected to an analog/digital converting unit 24 which comprises a plurality of amplifiers 241, resistors 242 and capacitors 243. Since the circuit of these electronic devices is the same as the general analog/digital convert circuit, therefore its structure will not be described here. The analog/digital converting unit 24 converts the inputted analog signal into a digital signal.

Further, the analog/digital converting unit 24 is connected to a microprocessor chip 25, and the microprocessor chip according to this preferred embodiment is a multitasking microprocessor chip (MCU). This microprocessor chip 25 is connected to a power supply unit 22, and the microprocessor chip 25 is connected to a display unit 26, an input unit 27, an alarm unit 28 and a storing unit 29; wherein the display unit 26 could be a liquid crystal display (LCD) module for displaying the result of the user's blood pressure measurement. Further, the input unit 27 could be a switch module comprised of more than one connected switches 271, and such switches 271 are individually connected to a resistor 272. Further, the alarm unit 28 is used for issuing a warning sound, and the storing unit 29 could be a memory for storing data.

Please refer to FIGS. 1, 2 and 3. The microprocessor chip 25 is connected individually to a driving device 30 and an air valve 40. The driving device 30 and air valve 40 are connected to a microprocessor chip 25 through a transistor 31, 41, and the driving device 30 and air valve 40 are connected to the airbag cuff 10. Further, the driving device 30 according to this embodiment is a motor, such that when the airbag cuff 10 is wrapped onto the user's wrist, the microprocessor chip 25 starts the driving device 30 to fill air into the airbag cuff 10 and inflate the airbag cuff 10 to press the blood vessels on the wrist. The driving device 30 will stop till the required pressure is achieved. Thus, a systolic pressure (high pressure) and a diastolic pressure (low pressure) are measured. At that time, the microprocessor chip 25 will turn on the air valve 40 to release the air inside the airbag cuff 10 to facilitate detecting the values of the systolic pressure (high pressure) and the diastolic pressure (low pressure).

Please refer to FIGS. 2, 3, 4, 4A and 5. The microprocessor chip 25 is connected to a 3D acceleration sensor chip 50, and the 3D acceleration sensor chip 50 comprises a semiconductor chip made of a piezoelectric transformer 51, a bridge type sensor 52 and a corresponding electronic device; wherein the piezoelectric transformer 51 has a plumb bob 511 thereon, and the plumb bob comprises a seating 512 which vibrates according to a change of the spatial position, and the seating 512 is connected to the bridge type sensor 52, so that the seating 512 moves as the user's arm moves. If the user's arm is inclined to different angles, the piezoelectric transformer 51 will produce a change of voltage. The value of the parameter for the change of voltage is sent to the microprocessor chip 25 via the bridge type sensor 52 and converted into a parameter for the spatial position. The microprocessor chip 25 will retrieve the predetermined values of the spatial position related parameters from the storing unit 29 and compare them with the detected values of the parameters. If the values of the detected parameters fall beyond the values of the predetermined range, then the spatial position of the measuring cuff worn on the wrist or the spatial position of the postures of the related part of the tester's body is incorrect and the alarm unit 28 will issue a sound until the tester moves the measuring cuff or change the posture of the user's body to the correct spatial position and the values of detected parameters fall within the values of the predetermined range. The alarm unit 28 will then stop, so that the user knows that the wrist or related part of the tester's body has been moved to the correct position.

Please refer to FIGS. 2, 3, 5, 5A and 5B. When the sphygmomanometer is in use, the adhesive member 11 ties the airbag cuff onto the user's wrist, and after the power supply unit 22 is turned on, the wrist tied with the sphygmomanometer starts raising and moving towards the position of the heart, so that the 3D acceleration sensor chip 50 inside the housing 20 moves according to the movement of the wrist and sends the obtained value to the microprocessor chip 25, and the microprocessor chip 25 will compare the original standard data stored in the storing unit 29 with the obtained data. If the values of detected parameters fall beyond the range, then the microprocessor chip 25 will instruct the alarm unit 28 to issue a sound to notice the tester and suggest the tester to move the wrist. The 3D acceleration sensor chip 50 will move according to the movement of the wrist and continuously sends the detected parameters to the microprocessor chip 25 and the microprocessor chip 25 continues the comparison until the values of the detected parameters fall within the predetermined range of the original stored parameters. Then, the alarm unit 28 will either stop or issue a different sound to notice the tester that the wrist has moved to a correct position. In the meantime, the microprocessor chip 25 will turn on the driving device 30 to pump air into the airbag cuff 10, so that the airbag cuff 10 is inflated to press the blood vessels on the wrist. As soon as the required pressure is reached, the driving device 30 will stop and then drive the pressure sensor 11 to perform the measurement. At that time, the microprocessor chip 25 starts the air valve 40 to release the air inside the airbag cuff 10 until the systolic pressure (high pressure) and diastolic pressure (low pressure) are measured. The results of the measurement will be displayed on the display unit 26 and saved in the storing unit 29.

In summation of the description above, the invention is novel on the shape, structure, and device, and since the invention uses the 3D acceleration sensor chip 5 for the positioning, the invention is applicable for different electronic sphygmomanometers including the desktop type, the wrist type, the tunnel type and the finger type, etc. Therefore, the present invention is more accurate and convenient than the prior art. The present invention herein enhances the performance than the conventional structure and further complies with the patent application requirements and is definitely a great idea for the products of this sort.

While the invention has been described by way of examples and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

The invention claimed is:

1. A sphygmomanometer with 3D positioning function, comprising:
    a pressure sensor for detecting a change in blood pressure, said pressure sensor having an amplifier and a bridge type sensor for amplifying and regulating a voltage in accordance with said blood pressure, and outputting an electric signal corresponding to said voltage;
    an analog/digital converting unit, coupled to said pressure sensor for said voltage, said analog/digital converting unit being capable of converting said electric signal from said pressure sensor into a digital signal;
    a microprocessor chip, coupled to said analog/digital converting unit for-processing said digital signal to obtain a result of a blood pressure measurement;
    a display unit, coupled to said microprocessor chip for displaying said result of said blood pressure measurement;
    an input unit, coupled to said microprocessor chip for inputting related settings;
    a storing unit, coupled to said microprocessor chip for storing setup data and said result of said blood pressure measurement;
    a driving device, coupled to said microprocessor chip for pumping air;
    an air valve, coupled to said microprocessor chip for releasing air;
    a 3D acceleration sensor chip, coupled to said microprocessor chip for producing a voltage according to a change in spatial position, the value of said voltage being converted into a digital parameter and said digital parameter being sent to said microprocessor chip to determine a correct position of at least said pressure sensor through processing by said microprocessor chip; and
    a power supply unit, coupled to said pressure sensor, microprocessor chip, display unit and input unit for supplying power to the pressure sensor, microprocessor chip, display unit, and input unit;
    wherein, when said spygmomanometer is in use, said acceleration sensor chip detects a spatial position of said pressure sensor and sends a parameter of said detected spatial position to said microprocessor chip, said microprocessor chip retrieving a predetermined value for related parameters from said storing unit and then comparing said parameter of said detected spatial position; wherein if said detected parameter falls beyond a predetermined range of said related parameters, then said measuring cuff is placed at an incorrect spatial position, and wherein if said detected parameters fall within said predetermined range of related parameters, a correct spatial position has been achieved, and said microprocessor chip controls said pressure sensor, driving device and air valve to perform said blood pressure measurement.

2. The sphygmomanometer with 3D space positioning function of claim 1, wherein said input unit is a switch module.

3. The sphygmomanometer with 3D space positioning function of claim 1, wherein said display unit is a liquid crystal display module.

4. The sphygmomanometer with 3D space positioning function of claim 1, wherein said storing unit is a memory.

5. The sphygmomanometer with 3D space positioning function of claim 1, wherein said microprocessor chip is coupled to an alarm unit for selectively issuing an alarm and a warning sound.

6. The sphygmomanometer with 3D space positioning function of claim 1, wherein said driving device is a motor.

* * * * *